(12) United States Patent
Yarnall et al.

(10) Patent No.: US 7,658,922 B2
(45) Date of Patent: Feb. 9, 2010

(54) MONOCLONAL ANTIBODIES, HYBRIDOMA CELL LINES, METHODS AND KITS FOR DETECTING PHYTASE

(75) Inventors: Michele Susan Yarnall, Research Triangle Park, NC (US); Lilian Zeitouni, Raleigh, NC (US)

(73) Assignee: AB Enzymes GmbH, Darnstadt (DE)

( * ) Notice: Subject to any disclaimer, the term of this patent is extended or adjusted under 35 U.S.C. 154(b) by 0 days.

(21) Appl. No.: 11/446,055

(22) Filed: Jun. 3, 2006

(65) Prior Publication Data

US 2006/0292636 A1 Dec. 28, 2006

Related U.S. Application Data

(60) Provisional application No. 60/693,818, filed on Jun. 24, 2005.

(51) Int. Cl.
- A61K 39/395 (2006.01)
- A61K 39/38 (2006.01)
- A61K 39/00 (2006.01)

(52) U.S. Cl. .............. 424/141.1; 424/130.1; 424/139.1; 424/146.1; 424/184.1; 424/274.1; 424/93.5; 435/4; 435/7.1; 435/7.31; 435/7.4

(58) Field of Classification Search .............. 424/130.1, 424/139.1, 141.1, 146.1, 184.1, 274.1, 93.5; 435/4, 7.1, 7.31, 7.4

See application file for complete search history.

(56) References Cited

U.S. PATENT DOCUMENTS

| | | | |
|---|---|---|---|
| 5,591,645 A | 1/1997 | Rosenstein | 436/514 |
| 5,876,997 A | 3/1999 | Kretz | |
| 6,110,719 A | 8/2000 | Kretz | |
| 6,183,740 B1 | 2/2001 | Short et al. | |
| 6,190,897 B1 | 2/2001 | Kretz | |
| 6,291,221 B1 | 9/2001 | van Loon et al. | |
| 6,358,722 B1 | 3/2002 | Van Loon et al. | |
| 6,699,704 B1 | 3/2004 | van Loon et al. | |
| 6,720,014 B1 | 4/2004 | Short et al. | |
| 6,855,365 B2 | 2/2005 | Short et al. | 426/656 |
| 7,078,035 B2 | 7/2006 | Short | |
| 7,135,323 B2 | 11/2006 | Lanahan | |
| 7,141,717 B2 | 11/2006 | Lanahan | |
| 2005/0009116 A1 | 1/2005 | Yarnell et al. | 435/7.9 |

FOREIGN PATENT DOCUMENTS

| | | |
|---|---|---|
| EP | 0 684 313 A | 11/1995 |
| EP | 0 897 985 A | 2/1999 |
| WO | WO 00/58481 | 10/2000 |
| WO | WO 01/90333 | 11/2001 |
| WO | WO 02/48332 | 6/2002 |
| WO | WO 03/057248 | 7/2003 |

OTHER PUBLICATIONS

Dassa et al, EBI [online] *Escherichia coli periplasmic phosphoanhydride phosphohydrolase (AppA) gene, complete cds*; retrieved Jan. 14, 2005 from EMBL; accession No. M58708.

Dassa et al, EBI [online] *Periplasmic appA protein precursor*; retrieved Jan. 14, 2005 from GenBank; accession No. P07102.

Dassa J., et al, The complete nucleotide sequence of the *Escherichia coli* gene appA reveals significant homology between pH 2.5 acid phosphatase and glucose-1-phosphatase. *Journal of Bacteriology*, vol. 172 (1990) pp. 5497-5500.

Lim et al, Crystal Structures of *Escherichia coli* Phytase and its Complex with Phytate *Nature Structural Biology*, vol. 11 No. 7 (Jul. 1, 1993) pp. 811-814.

Oh et al, *Catalytic Mechanism and Active Site Residues for a Phytate-Specific Thermostable Phytase from Bacillus amyloliqufaciens DS11* Abstracts of the General Meeting of the American society for Microbiology, vol. 100, May 22, 2000.

Pen et al, Phytase-Containing Transgenic Seeds as a Novel Feed Additive for Improved Phosphorus Utilization *Bio/Technology*, vol. 11, No. 7 (Jul. 1993) pp. 811-814.

Rodriguez et al, Site-Directed Mutagenesis Improves Catalytic Efficiency and Thermostability of *Escherichia coli* pH 2.5 Acid Phosphatase/Phytase Expressed in *Pichia pastorisArchives of Biochemistry and Biophysics*, vol. 382, No. 1 (Oct. 1, 2000) pp. 105-112.

Kim, Y-O et al. "High-level Expression of a recombinant thermostable phytase in *Bacillus subtilis*", Bioscience Biotechnology Biochemistry, Japan Soc. for Bioscience, Biotech. and Agrochem., Tokyo, JP vol. 63, No. 12, Dec. 1999 pp. 2205-2207.

Lehmann, Martin, et al., "From DNA sequence to improved functionality: Using protein sequence comparisons to rapidly design a thermostable consensus phytase," Protein Engineering, Oxford University Press, vol. 12, No. 1, Jan. 2000, pp. 49-57.

Syngetna Participations AG, International Application No. PCT/US06/023418, "*Written Opinion and Search Report*", Dec. 14, 2006.

*Primary Examiner*—Rodney P. Swartz
(74) *Attorney, Agent, or Firm*—Peter Corless; Christine C O'Day; Edwards Angell Palmer & Dodge LLP

(57) ABSTRACT

This invention relates to the field of immunology and more specifically relates to anti-phytase monoclonal antibodies, immunoassay methods, kits, and reagents, for the detection of a phytase from or derived from *E. coli* phytase, in particular, Quantum™ phytase. The invention further relates to hybridoma cell lines that produce anti-phytase monoclonal antibodies.

33 Claims, 7 Drawing Sheets

1. Fill tube up to the 15 mark.
2. Add feed to the extraction bag.
3. Add extraction buffer to the bag.

4. Wait 10 min, then cut bag in half.
5. Remove extract with the pipet.
6. Add a few drops to the sample well.

7. Wait 5 min and then read the results.

MONOCLONAL ANTIBODIES, HYBRIDOMA CELL LINES, METHODS AND KITS FOR DETECTING PHYTASE

This application claims the benefit of the filing date of U.S. Provisional Patent Application No. 60/693,818, filed on Jun. 24, 2005, which is hereby incorporated by reference.

FIELD OF THE INVENTION

This invention relates to the field of immunology and more specifically relates to monoclonal antibodies, immunoassay methods, including ELISA and immunostrip assays, kits and reagents, for the detection of phytase. The invention further relates to hybridoma cell lines that produce anti-phytase monoclonal antibodies.

BACKGROUND OF INVENTION

There is a significant need for a convenient, relatively easy assay for detecting the presence of phytase in animal feed. There is also a tremendous need for determining whether a plant has been genetically modified or whether grain or processed foods contain GMO traits. The need requires test methods that can detect and quantitate either the novel DNA or protein. The present inventions meet this need by providing monoclonal antibodies, hybridoma cell lines, immunological methods, reagents and kits for detection and quantification of phytase.

SUMMARY OF THE INVENTION

Methods, kits, and reagents for detecting and measuring phytase in a sample are provided. In particular, the phytase is a bacterial phytase, more specifically an *E. coli* phytase, and more particularly, Quantum™ phytase. The phytase is produced in various micro-organisms, including but not limited to *Esherichia coli, Schizosaccharomyces pombe*, and *Pichia pastoris* or in plants, including but not limited to maize, wheat, rice, canola, and alfalfa, for example. In particular, the phytase is detected in feed or in genetically modified plants containing a gene encoding the protein. The feed is animal feed. The animal feed may be for monogastrics or ruminants. The feed may be mash feed and/or pelleted feed.

The reagents include purified protein and antibodies specific for the phytase. The phytase protein may be isolated from *E. coli* inclusion bodies and administered to animals to produce polyclonal or monoclonal antibodies. Alternatively, the protein may be isolated from a soluble cell extract, such as an *E. coli* cell extract.

The antibodies have high sensitivity and specificity for the phytase and are useful in immunoassay methods for the detection of enzymatically active phytase in animal or in genetically modified organisms.

The methods are immunoassays employing the monoclonal antibodies described herein and are capable of detecting low concentrations of phytase. The antibodies are purified and therefore react minimally with other proteins that may be present in the sample. The antibodies and/or protein are assembled in a kit with conventional immunoassay reagents for detection of the phytase.

In view of the above, there is a real need for the development of technology that will allow the identification of specific phytases in samples.

BRIEF DESCRIPTION OF THE DRAWINGS

FIG. 5A shows the three immunostrips with nitrocellulose coated with monoclonal PHY46 antibodies as the coating antibody (labeled as Monoclonal #46); figure 5B shows the three immunostrips with nitrocellulose coated with monoclonal PHY36 as the coating antibody (labeled as Monoclonal #36) and FIG. 5C shows the immunostrips with nitrocellulose coated with monoclonal PHY37 as the coating antibody (labeled as Monoclonal #37). Monoclonal anti-phytase antibodies PHY46, PHY36 and PHY37 were used as the coating antibodies. Gold conjugated monoclonal PHY34 was used as the labeled antibody for the detection for all immunoassays.

FIG. 8A—grind 300 g of feed in coffee grinder; 8B—add 80 ml extraction buffer to 20 g sample; 8C—shake vigorously for 1 minute; 8D—let container sir for 30 minutes; 8E—set up plate and reagents and bring to ambient temperature; 8F—add 50 ul of controls or samples to wells; 8G—add 50 ul of conjugate to wells and incubate for 30 minutes; 8H—wash wells 5 times with distilled water; 8I—add 100 ul of substrate to wells and incubate 15 minutes; 8J—interpret the results visually or read at 650 nm in a plate reader and 8K—shows representative results.

DETAILED DESCRIPTION OF THE DISCLOSED EMBODIMENTS

Figure 1:
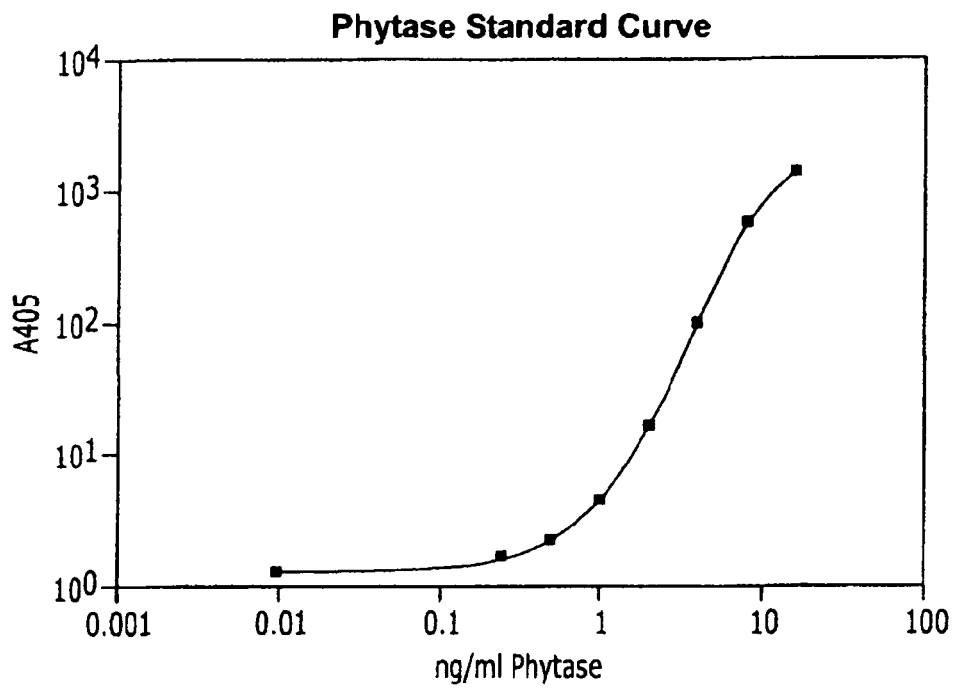
FIG. 1 is a graph showing a standard curve for phytase activity.

Methods, kits, and reagents for the detection of phytase in a sample are described herein. Monoclonal cell lines producing anti-phytase monoclonal antibodies are also described.

The methodology of the invention may be used to detect any enzyme in samples such as animal feed. Many feed enzymes are known to those skilled in the art. For example, a number of phytases are known, the detection of which may be accomplished using the present invention. Known phytases include, but are not limited to, those described in WO 01/90333, entitled "Recombinant Bacterial Phytases and Uses Thereof;" WO 99/08539, entitled "Novel Phytase;" U.S. Application Publication No. 20030157646, entitled "Microbially Expressed Thermotolerant Phytase For Animal Feed", and U.S. Appl. Publication No. 20030170293, entitled "Thermotolerant Phytase for Animal Feed," each and all of which are incorporated by reference herein in their entirety.

It is important when making immunoassays to detect phytase in transgenic plants and the products produced from them (including food fractions), that a test has the capacity to detect the specific protein. Thus, highly specific antibodies are very important for development of successful commercial products.

The reagents are antigenic phytase and anti-phytase antibodies that are highly specific for the phytase. The method is an immunoassay for the sensitive, specific detection of phytase, specifically for the detection of phytase in animal feed and in genetically engineered plants, such as agricultural products. The kit contains the anti-phytase antibodies described herein and other reagents, particularly those used in a strip test format, for use in the immunoassay described in more detail below.

Antigenic Protein

For preparation of recombinant protein, such as phytase, following transformation of a suitable host strain and growth of the host strain to an appropriate cell density, e.g., a bacterial, insect or yeast host, a selected promoter may be induced by appropriate means (e.g., temperature shift or chemical induction) and cells cultured for an additional period to yield recombinant enzyme. Cells are then typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

The phytase enzyme is recovered and purified from recombinant cell cultures by methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

Antibodies

Antibodies useful in the invention may be made using a rabbit, chicken, mouse or a goat. The program for inoculation is not critical and may be any normally used for this purpose in the art. Such procedures are described, for example, in *Antibodies A Laboratory Manual*, Cold Spring Harbor Laboratory, 1988, pages 92-115.

The preferred antibodies for the detection of phytase are rabbit antibodies, chicken antibodies, and goat antibodies that are immunoaffinity purified against recombinant phytase produced in *E. coli* inclusion bodies or mouse monoclonal antibodies. To detect and quantitate phytase, the antibodies are labelled, preferably, directly using labels which include enzymes, radioisotopes, and colored particles such as latex beads or colloidal gold. In another embodiment, the antibodies are indirectly labelled, for example, by reaction with labelled substances that bind to the antibody such as secondary antibodies, protein A or protein G.

Polyclonal Antibodies

In one embodiment, the antibodies are polyclonal antibodies. Methods for preparing polyclonal antibodies are known to the skilled artisan. Polyclonal antibodies can be raised in an animal, for example, by one or more injections of an immunizing agent and, if desired, an adjuvant. Typically, the immunizing agent and/or adjuvant will be injected in the mammal by multiple subcutaneous or intraperitoneal injections. The immunizing agent includes the feed enzyme or fusion protein thereof For example, the agent is the phytase polypeptide or a fusion protein thereof.

Examples of adjuvants include Freund's complete adjuvant and MPL-TDM adjuvant (monophosphoryl Lipid A, synthetic trehalose dicorynomycolate). The immunization protocol can be selected by one skilled in the art without undue experimentation. The preferred antibodies are highly sensitive for the detection of phytase proteins, for example transgenic phytase proteins at relevant concentrations in bulk samples of commodity grain in the distribution channel. Preferably, the antibodies detect phytase protein at a high sensitivity of approximately 0.059 ng/ml. High sensitivity antibodies are useful for detection of low concentrations of phytase proteins in genetically engineered crop tissues, such as, but not limited to, leaf, stem, seed, stalk, root, and the like, or products derived from such crops, such as food fractions or animal feed.

Monoclonal Antibodies

The anti-phytase antibodies were; monoclonal antibodies. Monoclonal antibodies were prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The monoclonal antibodies of the invention were made according to the description of Example 6. The hybridoma cell lines were deposited on Nov. 3, 2004 and Feb. 2, 2005 (as indicated below), according to the Budapest Treaty at the DSZM-Deutsche Sammlung von Mikrooranismen und Zellkuturen GmbH, Mascheroder Weg 1b, D-38124 Braunschweig, Germany. The cell lines have been assigned the following Accession Numbers:

| Cell culture PHY34 | DSM ACC2698 | Deposit Mar. 11,2004 |
|---|---|---|
| Cell Culture PHY36 | DSM ACC2699 | Deposit Mar. 11,2004 |
| Cell Culture PHY37 | DMS ACC2700 | Deposit Mar. 11,2004 |
| Cell Culture PHY46 | DSM ACC2701 | Deposit Mar. 11,2004 |
| Cell Culture Phytase Mab 28 | DSM ACC2715. | Deposit Feb. 2,2005. |

The monoclonal cell lines of the invention were made according to the description in Example 6, infra.

The immunizing agent typically includes the desired polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells are cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically includes hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al., *Monoclonal Antibody Production Techniques and Applications*, Marcel Dekker, Inc., New York, 1987, pp. 51-63).

The culture medium in which the hybridoma cells are cultured is then assayed for the presence of monoclonal antibodies directed against PRO. Preferably, (he binding specificity of monoclonal antibodies produced by the hybridoma cells is determined by immuno-precipitation or by an in vitro binding assay, such as radio-immunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones are subcloned by limiting dilution procedures and grown by standard methods (Goding, supra). Suitable culture media for this purpose includes, for example, Dulbecco's Modified Eagle's Medium and RPMI-1640 medium. Alternatively, the hybridoma cells are grown in vivo as ascites in a mammal. The monoclonal antibodies secreted by the subclones are isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies are also be made by recombinant DNA methods, such as those described in U.S. Pat. No. 4,816,567. DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA is placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also is modified, for example, by substituting the coding sequence for human heavy and light chain constant domains in place of the homologous murine sequences (U.S. Pat. No. 4,816,567; Morrison et al., supra), or by covalently joining to the immunoglobulin coding sequence to all or part of the coding sequence for a non-immunoglobulin polypeptide. Such a non-immunoglobulin polypeptide is substituted for the constant domains of an antibody of the invention, or is substituted for the variable domains of one antigen-combining site of an antibody of the invention to create a chimeric bivalent antibody.

In another embodiment, the antibodies are monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

Other methods known in the art include the method of Kearney, et al., J. Immunol. 123: 1548-1558 (1979), which is incorporated by reference herein. Briefly, animals such as mice or rabbits are inoculated with the immunogen in adjuvant, and spleen cells are harvested and mixed with a myeloma cell line. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce anti-phytase monoclonal antibodies. Hybridomas producing antibodies are cloned, expanded and stored frozen for future production.

In another embodiment, the antibody is labelled directly with a detectable label for identification and quantitation of a phytase protein. Labels for use in immunoassays are generally known to those skilled in the art and include, but are not limited to enzymes, radioisotopes and fluorescent, luminescent and chromogenic substances including colored particles such as colloidal gold and latex beads.

Alternatively, the antibodies are labelled indirectly by reaction with labelled substances that have an affinity for immunoglobulin, such as protein A or G or second antibodies. The antibodies are conjugated with a second substance and detected with a labelled third substance having an affinity for the second substance conjugated to the antibody. For example, the antibody is conjugated to biotin and the antibody-biotin conjugate detected using labeled avidin or strepavidin.

In another embodiment, the antibody is conjugated to a hapten and the antibody-hapten conjugate detected using labelled anti-hapten antibody. These and other methods of labelling antibodies and assay conjugates are well known to those skilled in the art.

Immunoassay

The antibodies are collectively assembled in a kit with conventional immunoassay reagents for detection of the phytase using the immunoassay described below. The kit may optionally contain both monoclonal and polyclonal antibodies and a standard for determining the presence of the phytase in a sample. The kit containing these reagents provides for simple, rapid, on site detection of the protein.

The antibodies described above are used as the basic reagents of a number of different immunoassays to determine the presence of the phytase in a sample. The antibodies are employed in any type of immunoassay, whether qualitative or quantitative.

In a typical quantitative sandwich assay, there are three basic parts. For example, in such as assay for phytase, the phytase protein in a genetically modified plant extract or feed extract, such as chicken feed, is captured onto the solid phase using a primary antibody. In one embodiment, the primary antibody is a rabbit anti-phytase antibody. Then a "sandwich" is formed between the primary antibody, the phytase protein, and the secondary antibody that has been added to the well. In one embodiment, the secondary antibody is a goat anti-phytase antibody. After a wash step, where unbound secondary antibody has been removed, the bound secondary antibody is detected using a labelled antibody. In a particular embodiment, the detection antibody is an alkaline phosphatase-labelled donkey anti-goat antibody. Substrate for the detection enzyme, alkaline phosphatase, is added and color development is measured by reading the absorbance of each well. The standard curve uses a four-parameter curve fit to plot the concentrations versus the absorbance.

More generally, the immunoassay for the detection of phytase comprises the steps of: a) preparing an extract of the sample; b) incubating a portion of the extract with a primary anti-phytase antibody which binds to the phytase, the primary antibody being bound to a solid carrier, and a secondary anti-phytase antibody which binds to the phytase to create an antibody-phytase-antibody complex, c) washing the antibody-phytase-antibody complex to remove unbound secondary antibody; d) adding a detection antibody that immunologically reacts with the secondary antibody wherein the detection antibody is labelled; and e) measuring the amount of bound labeled antibody to determine the concentration of the phytase.

In one embodiment, the phytase is a bacterial phytase, more particularly, an E. coli phytase. In an even more particular embodiment, the phytase is a thermostable phytase, such as Quantum™ phytase.

In another embodiment of the invention, the detectable label is an enzyme. In more preferred embodiments, the enzyme is alkaline phosphatase, peroxidase, or β-galactosidase. In another embodiment, the enzyme produces an soluble reaction product. The invention also provides a kit for the detection and quantification by the immunoassay method comprising: a) a means of extracting the phytase from a sample; b) a solid support comprising a primary anti-feed enzyme antibody bound to the solid support; c) a secondary anti-phytase antibody; and d) a detection antibody capable of immunologically binding to the secondary antibody and wherein the detection antibody is labelled with a means of detection.

In a particular embodiment, the means of detection is an enzyme. In particular embodiments, the detection enzyme is alkaline phosphatase, peroxidase, or β-galactosidase. In another embodiment, the enzyme produces a soluble or an insoluble reaction product. In another embodiment, the kit further comprises a substrate for the enzyme. Such immunoassays are also referred to enzyme-linked immunosorbent assays (ELISA).

The antibodies described above are also employed in a qualitative immunoassay for the detection of a feed enzyme, such as phytase. One such assay is commonly referred to as an immunostrip. An immunostrip is produced using membranes and filters through which a liquid sample is drawn by capillary action. The phytase in the sample reacts with the antibodies contained in the immunostrip as it moves the length of the strip. To detect phytase protein in chicken feed, the feed is washed with a buffer, separated from the solid material, and added to the immunostrip. As the liquid sample migrates to the opposite end of the immunostrip, the phytase reacts with the specific antibodies and is captured in a line that becomes visible. Detection of the signal on the test line indicates that phytase is in the sample.

In one embodiment the invention provides an immunoassay for the detection of phytase in a sample comprising the steps of: a) preparing an extract of the sample in the presence of a primary antibody which immunologically recognizes phytase in the extract such that a primary antibody-phytase complex is formed; b) preparing a solid phase format having a significant measurement in three dimensions to form a substantial volume with a plurality of interstitial spaces by binding to it a desired secondary antibody capable of immunologically recognizing phytase and wherein the secondary antibody is conjugated to a means of detection and wherein the secondary antibody also immunologically recognizes phytase; d) combining the extract of step (a) with the prepared format of step (b) whereby the extract is drawn through the interstitial spaces of the prepared solid phase format capturing the primary antibody-phytase complex; e) detecting phytase by the presence of said captured primary antibody-phytase complex.

In one embodiment the phytase is a bacterial phytase. In a more particular embodiment, the phytase is from E. coli. In another embodiment, the phytase is a thermostable phytase, such as but not limited to, Quantum™ phytase.

In other embodiments, the solid phase format is cellulose acetate, cellulose, nitrocellulose or nylon. In another embodiment, the solid phase format is composed of multiple stacked and contiguous layers wherein each layer is capable of capturing a different feed enzyme. In a preferred embodiment, the solid phase support further comprises a sample absorption pad of the solid phase format. In a more preferred embodiment, the immunoassay further comprises a strip comprising a labelled anti-feed enzyme antibody.

In a particular embodiment, the means of detection is colloidal gold.

A highly sensitive immunoassay employing the antibodies described above is provided. The assay is useful for detection of a phytase enzyme in a feed sample. Also, the assay is useful for the detection of genetically modified organisms that have been engineered to include a gene encoding a phytase gene. The immunoassay is capable of detecting low concentrations of the protein in samples, such as animal feed and in genetically enhanced crop samples.

As described above, the antibodies used in the immunoassay are immuno-reactive with epitopes or a common epitope on the phytase protein, expressed by various micro-organisms and react minimally with other proteins that may be present in the sample, thus providing for an accurate determination of the presence of a genetically modified organism in a sample, such as a grain sample.

The immunoassay is useful for detecting the presence or amount of a phytase, in a variety of samples, including animal feed and agricultural samples such as plant material. The sample may be obtained from any source in which the desired protein is accessible to the antibody. For example, the sample may be any plant tissue or extract including root, stem, stalk, leaf, or seed or products derived from such crops, such as food fractions.

One or more of the antibodies described above are employed in any heterogeneous or homogeneous, sandwich or competitive immunoassay for the detection of phytase protein. Either the antibody is labelled with a detectable label or coupled to a solid phase. Methods for coupling antibodies to solid phases are well known to those skilled in the art. In accordance with the immunoassay method, the sample containing phytase is reacted with the antibody for a sufficient amount of time under conditions that promote the binding of antibody to phytase protein in the sample. It will be understood by those skilled in the art that the immunoassay reagents and sample may be reacted in different combinations and orders. A physical means is employed to separate reagents bound to the solid phase from unbound reagents such as filtration of particles, decantation of reaction solutions from coated tubes or wells, magnetic separation, capillary action, and other means known to those skilled in the art.

It will also be understood that a separate washing of the solid phase may be included in the method.

The concentration of phytase protein in the sample is determined by comparing the intensity of the color produced by the sample to a color card, by using a reflectometer, or by using a spectrophotometer or microtiter plate reader.

The resulting reaction mixture, or combination of antibody and sample, is prepared in a solution that optimizes antibody-phytase binding kinetics. An appropriate solution is an aqueous solution or buffer. The solution is preferably provided under conditions that will promote specific binding, minimize non-specific binding, solubilize the feed enzyme, stabilize and preserve reagent reactivity, and may contain buffers, detergents, solvents, salts, chelators, proteins, polymers, carbohydrates, sugars, and other substances known to those skilled in the art.

The reaction mixture solution is reacted for a sufficient amount of time to allow the antibody to react and bind to the phytase protein to form an antibody-phytasecomplex. The shortest amount of reaction time that results in binding is desired to minimize the time required to complete the assay. An appropriate reaction time period for an immunostrip test is less than or equal to 10 minutes or between approximately one minute and 10 minutes. A reaction time of less than five minutes is preferred. Most preferably, the reaction time is less than three minutes. By optimizing the reagents, binding may be substantially completed as the reagents are combined.

The reaction is performed at any temperature at which the reagents do not degrade or become inactivated. A temperature between approximately 18° C. and 30° C. is preferred, and most preferred reaction temperature is ambient or room temperature (approximately 22° C.).

A solid phase format such as an immunostrip is ideally suited for this immunoassay. Test strips are comprised of multiple porous components, membranes and filters, through which liquid sample is drawn by capillary action. The phytase in the sample reacts with the test reagents contained within the test strip as it traverses the length of the strip. To detect protein in grain or seed, the grain is ground into a powder and the protein extracted from the powder with a liquid that is then separated from the solid material and assayed using the test. The liquid is applied to the immunostrip, and the phytase protein migrates toward the distal end of the strip. As it migrates down the strip, the phytase reacts with reagents applied to or immobilized on the strip causing a detectable signal product. Detection of the signal indicates the presence of phytase in the sample.

In one embodiment the solid phase format is cellulose acetate, cellulose, nitrocellulose or nylon. In a preferred embodiment, the solid phase format is nitrocellulose.

In another embodiment, the solid phase format comprises a sample absorption pad, a strip of nitrocellulose and a bottom pad comprising a labelled anti-phytase antibody.

Enzyme Linked Immunosorbent Assay (ELISA)

Serological methods that are used are based on the enzyme-linked immunosorbent assay (ELISA) techniques are described in, for example, Harlow, E., Lane D., Antibodies: a Laboratory Manual. 1998. Cold Spring Harbor Laboratory. pp 553-612. The ELISA method used in the present invention is described in Example 1.

Immunoassay Kit

An immunoassay kit for the detection of feed enzyme protein in a sample contains one or more of the antibodies described above. The kit may additionally contain equipment for obtaining the sample, a vessel for containing the reagents, a timing means, a buffer for diluting the sample, and a calorimeter, reflectometer, or standard against which a color change may be measured. The kit may include the reagents in the form of an immunostrip as described above.

In a preferred embodiment, the reagents, including the antibody are dry. Addition of aqueous sample to the vial or strip results in solubilization of the dry reagent, causing it to react.

The reagents, immunoassay methods, and kits described above will be further understood with reference to the following non-limiting examples. The examples below show typical experimental protocols and reagents that can be used in the detection of phytase in samples such as feed or other plant materials. Such examples are provided by way of illustration and not by way of limitation.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Numerous references cited above are all incorporated herein in their entireties.

EXAMPLES

These methods and materials describe the general procedure for preparing the corn or feed samples and the production of the polyclonal and monoclonal antibodies used in the examples described below.

Materials and Methods

Maize Sample: The corn extract was derived from either Hi II seed or A188 seed (non-transgenic) or genetically modified phytase seed. Five kernels were pulverized using a KLECO tissue grinder. The resulting corn flour was suspended in 5 mls distilled water to solubilize the proteins. The supernatant was tested in either the ELISA or with the immunostrips.

Production of Polyclonal Antibodies

For immunization: After the initial injection, the animal (rabbit or goat) is boosted after 28 days. Each subsequent boost thereafter is every 21 days. The animals are bled 10 days after each boost.

For chickens, the first boost is 7 days after the initial injection, followed by boosts every 28 days. The chickens are bled 10 days after each boost, and if a good antibody titer is detected, the eggs laid after the boost are collected.

The immunizing agent was the entire phytase protein purified from an *E. coli* expression system. With the first injection into the animal, the protein is emulsified in complete Freund's adjuvant. The boosts are in incomplete Freund's adjuvant. The animals used to produce the polyclonal antibodies are rabbit, chicken, and goat.

Phytase (Nov9X) Purification:

Phytase (Nov9X) formulated with 10% sorbitol, 10% NaCl, and pH 4.2 was dialyzed overnight against 25 mM Tris-HCl, pH 8.0 at 4° C. using SnakeSkin 10K MWCO dialysis tubing (Pierce, Rockford, Ill.). Following dialysis solid $(NH_4)_2SO_4$ was added to the phytase mixture, initially to 25% saturation, then to 50% and finally 75% saturation at 0° C. Upon the addition of $(NH_4)_2SO_4$ to 25% saturation the mixture was stirred for 30 minutes at 0° C., then centrifuged at 20,000 rpm for 20 minutes. To the decanted supernatant, $(NH_4)_2SO_4$ was added to 50% saturation while the pellet was resuspended in 25 mM Tris-HCl, pH 9.0. This procedure was carried out 3 times yielding Nov9X $(NH_4)_2SO_4$ pellets of 0-25%, 25-50%, and 50-75% saturation. SDS-PAGE analysis demonstrated the presence of Nov9X in the 50-75% fraction. This fraction was dialyzed against 25 mM Tris-HCl, pH 9.0 and prepared for column chromatography purification.

Crude Nov9X TAM from the 50-75% $(NH_4)_2SO_4$ fractionation was loaded onto a HiTrapQ anion exchange column (Amersham Biosciences, Piscataway, N.J.) using a flow rate of 5.0 mL/min. A linear gradient of 0-0.4 M NaCl in 25 mM Tris-HCl, pH 9.0 developed over 30 minutes was used to elute Nov9X. Absorbance measurements at 280 nm were used to follow the progress of the chromatography run. Following SDS-PAGE analysis the purest of the Nov9X containing fractions were pooled, concentrated with a Centricon Plus-20 centrifugal concentrator (Millipore, Bedford, Mass.), and loaded onto a 26/60 Sephacryl S100 size exclusion column (Amersham Biosciences, Piscataway, N.J.) run at 1 mL/min. The eluant buffer was 25 mM Tris-HCl, pH 9.0. Fractions containing pure Nov9X were pooled, concentrated, dialyzed against 25 mM Tris-HCl, pH 8.0, and used for the studies described below.

Example 1

Phytase ELISA

This example describes the detection and quantitative measurement of phytase enzyme in a corn sample using the ELISA immunological technique.

Procedure

The multiwell plates (Nunc, Maxisorp) were coated at 4° C. overnight with the rabbit anti-phytase antibody at a concentration of 2 µg/ml, diluted in 50 mM sodium borate/boric acid, 75 mM NaCl, pH 8.5. The plates were washed five times with 10 mM Tris containing 0.05% Tween-20 and 0.03% sodium azide pH 8. wash buffer). Note: the same wash step was performed after each incubation period to remove unbound antibodies/samples. Plates were then blocked for 45 min. at room temperature with 1% bovine serum albumin, 0.05% Tween-20, 0.03% sodium azide, 150 mM NaCl in 100 mM sodium phosphate, pH 7.4 diluent). Fifty microliters of each sample was added to the plate and incubated for 1.5 hr at room temperature. The goat anti-phytase antibody (diluted to 2 µg/ml in diluent) was added to the plates and incubated for 1 hr at 37° C. The detection antibody (alkaline phosphatase-labelled donkey anti-goat antibody was diluted to 1 µg/ml in diluent) was added to the plates and incubated for 1 hr at 37° C. The substrate, paranitrophenylphosphate (pNPP) was added and allowed to develop for 30 min at room temperature. The absorbance was measured at 405 nm with 492 nm as a reference.

Assay Characteristics

The phytase standard curve was a 4-parameter curve fit (see FIG. 1). The curve was plotted linear vs. log with a range from 0.04 to 16 ng/ml. To plot the 4-parameter standard curve on a log X axis, the 0 ng/ml standard must be entered into the analysis program at 0.01 ng/ml instead of 0 ng/ml. The analysis program used was WinSelect™ software for the Tecan Sunrise™ microplate reader, although any four-parameter curve-fitting program will work.

The minimum detectable dose (MDD) was the lowest level of phytase protein that was statistically distinguished from the zero standard. The minimum detectable dose was determined by analysis of 24 replicates of negative control corn seed extract at 1 mg/ml total protein. Two standard deviations of the zero standard mean O.D. (95% confidence limits) were added to the mean, and the dose of this total O.D. value was determined using a standard curve. The minimum detectable dose was 0.044 ng/ml.

Between-run precision was determined by assaying 4 different control samples in 21 different assays. The samples were purified phytase spiked into ELISA diluent. The results are set forth below in Table 1. The precision is good, less than 15%, for samples concentrations that are measured in the linear portion of the standard curve.

TABLE 1

Between-run Precision Test

| Sample | Mean Phytase ng/ml | Standard Deviation | % Coefficient of Variation |
|---|---|---|---|
| 1 | 9.65 | 2.27 | 23.5% |
| 2 | 2.99 | 0.38 | 12.8% |
| 3 | 0.94 | 0.11 | 12.0% |
| 4 | 0.39 | 0.10 | 25.6% |

Within-run precision was determined by testing 20-24 replicates of the following samples. The samples were phytase spiked into ELISA diluent. The results are set forth in Table 2 below. All samples resulted in very good precision, indication good reproducibility within a single assay run.

TABLE 2

Within-run Precision Test

| Sample | Mean Phytase ng/ml | Standard Deviation | % Coefficient of Variation |
|---|---|---|---|
| 1 | 0.463 | 0.030 | 6.44% |
| 2 | 2.293 | 0.264 | 11.51% |
| 3 | 5.224 | 0.787 | 15.07% |

Four corn seed extracts were diluted with ELISA diluent in order to test the linearity of the assay. The corn extract was derived from either Hi II seed or A188 seed (non-transgenic) or genetically modified phytase-producing seed. Five kernels were pulverized using a KLECO tissue grinder (Visalia, Calif.). The resulting corn flour was suspended in 5 mls distilled water to solubilize the proteins. The supernatant was tested in either the ELISA or with the strips. The percent recovery of phytase from the diluted samples was acceptable.

TABLE 3

Linearity of Assay Test

| Sample | Dilution | Measured Phytase (ng/ml) | Measured Value X dilution faction | Percent Recovery |
|---|---|---|---|---|
| A | 1/2500 | 12.76 | 31900 | 82% |
|  | 1/5000 | 5.85 | 29250 | 75% |
|  | 1/10,000 | 3.90 | 39000 | 100% |
| B | 1/2500 | 6.87 | 17175 | 52% |
|  | 1/5000 | 6.90 | 34500 | 104% |
|  | 1/10,000 | 3.33 | 33300 | 100% |
| C | 1/2500 | 3.58 | 8950 | 63% |
|  | 1/5000 | 2.35 | 11750 | 83% |
|  | 1/10,000 | 1.41 | 14100 | 100% |
| D | 1/2500 | 6.11 | 15275 | 72% |
|  | 1/5000 | 3.54 | 17700 | 83% |
|  | 1/10,000 | 2.13 | 21300 | 100% |

Example 2

Phytase Immunostrips

This example describes the use of Immunostrip assays to test the presence of phytase in a sample.

Procedure

Extracts of mashed chicken feed were prepared by adding feed to a 50 ml centrifuge tube up to the 15 ml designation. This amount of feed was added to one side of the mesh insert within the extraction bag. Extraction buffer (25 ml of 0.1 M borate pH 7.5 containing 0.5% Tween-20) was added and the buffer was gently pressed over the feed to ensure that all the feed was wet. The extract was incubated at room temperature for at least 10 min before applying 3-5 drops to the immunostrip for testing.

Immunostrip

Briefly, the lateral-flow immunostrip comprised a detection membrane of nitrocellulose (2.5×18 cm), supported on a plastic backing (G&L Precision Die Cutting, Inc, San Jose, Calif.), in which a 1 mm line of specific rabbit (chicken antibodies can also be used) anti-phytase polyclonal antibody was sprayed. A reagent control line of donkey anti-goat antibody was sprayed in parallel above the first antibody line. The bottom end portion of the strip of nitrocellulose is overlayered with a piece of polyester strip. The polyester strip is first treated with 0.5% BSA, 0.5% polyvinylalcohol and 0.1% Triton X-100; 50 mM phosphate buffer pH 7.4 and the colloidal gold conjugated goat anti-phytase antibody. The polyester strip is allowed to dry. The polyester strip is then overlayered with a sample application pad of cotton. The sample application pad was also pretreated 0.1% Triton X-100 in 0.1 M borate buffer pH 8.5 and allowed to dry. Flanking the other end or top end of the nitrocellulose strip is another cotton pad to absorb the solution from the sample after it passes over the test antibody and control antibody areas on the nitrocellulose. This completed card was then cut into 4 mm test strips to fit into a plastic cassette with an oval sample application well positioned above the sample pad and a rectangular detection window positioned above the detection area of the nitrocellulose membrane.

Figure 3:
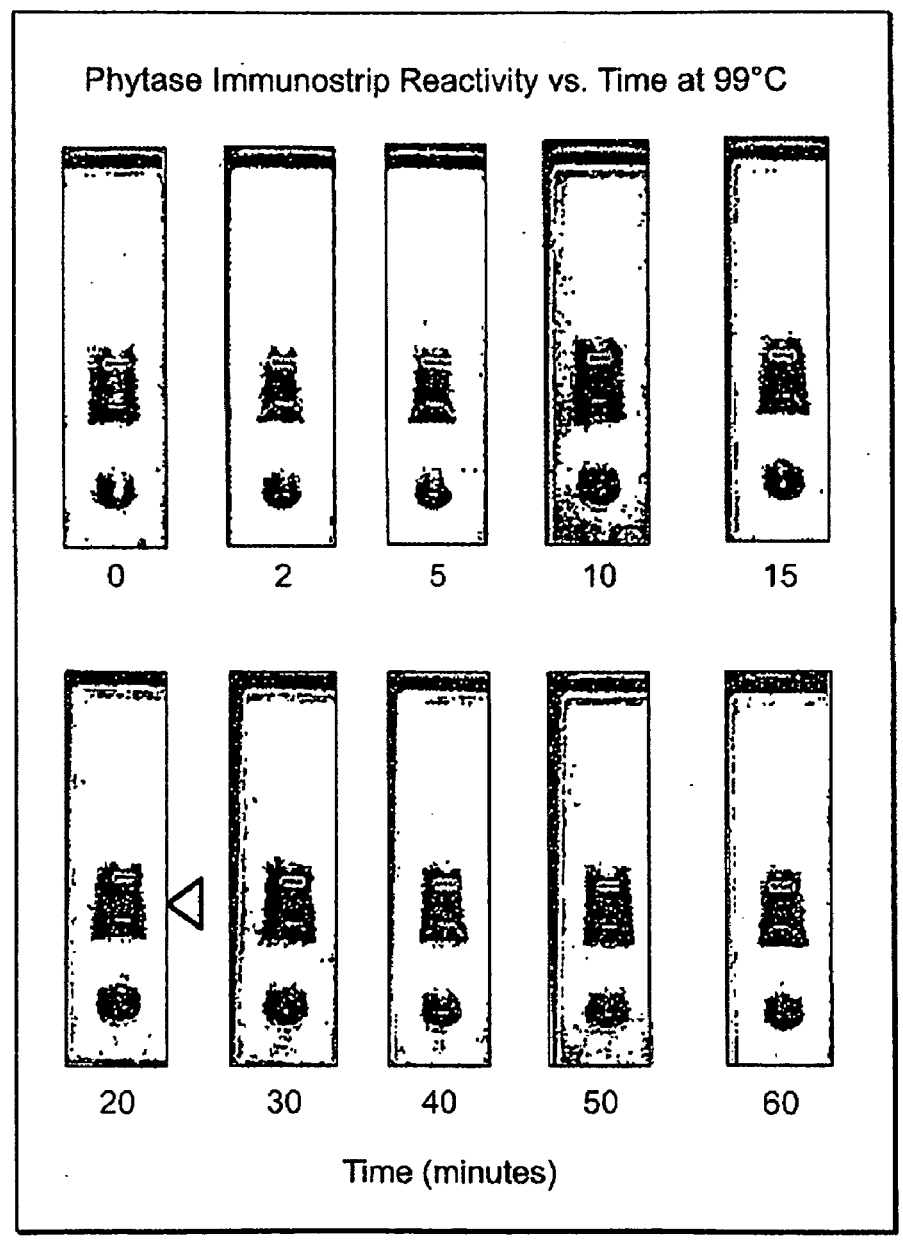
FIG. 3 is a scanned reproduction of immunostrip tests showing the detection of phytase (arrow) after incubation at 99° C. for up to one hour. A decrease in the detection of phytase is seen after about 20 minutes at 99° C.
Figure 4:
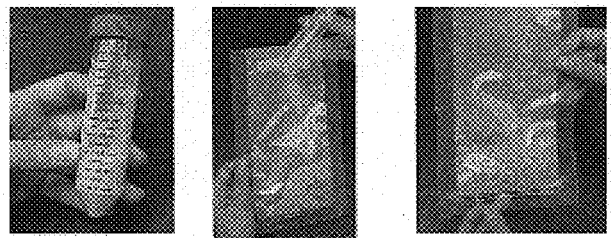
FIG. 4 is a depiction of an exemplary immunoassay test kit and the method of using the same.
Figure 4:
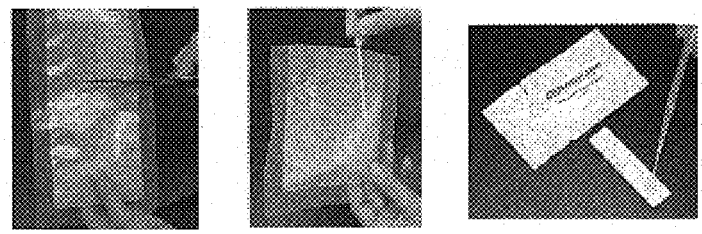
Figure 4:
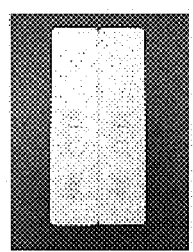
Figure 4:
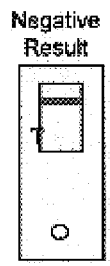
Figure 4:
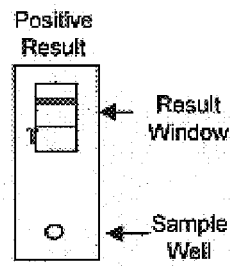

The assay was performed by adding 150 µl (3-5 drops) of extract to the sample well. After waiting approximately 5-10 minutes, the results appeared in the result window. If phytase was present in the sample, a double red line appeared in the result window. The lower line indicates the presence of phytase while the upper line is the control line demonstrating a properly working device. If phytase is absent, only one single red control line appears in the result window. See FIGS. 3 and 4 for sample immunostrips. FIG. 3 shows the detection of the presence of phytase. The detection of phytase decreases after 20 minutes as indicated by the arrow, because that is when the phystase is starting to lose activity.

Detailed Preparation of the Immunostrip

Phytase $2^{nd}$ Generation Strips—Coating of Membrane Materials

Coating the test line: Absorbant material cards, 2.25 in×180 mm with AE100 membrane are coated with chicken anti-phytase IAP at 0.1 mg/ml in PBS using a Camag™ sprayer set at a volume to 18 (1 µl/cm). The card is placed on a platform and the portion of the card with the 2 paper pieces is placed closest to the front of the instrument. The card is secured with magnets. Fill the syringe with 1.0 mg/ml chicken anti-phytase IAP.

Coating the control line: A control line of donkey-anti-goat antibody is used as a control line on the immunostrip. The control line is sprayed on the cards using a Camag™ sprayer set with the volume to 18 (1 µl/cm). The cards are dried at 33° C. overnight, then transfer to room temperature and stored desiccated at room temperature. Phytase Strips—Coating the Conjugate onto Polyester Procedure The gold conjugate was diluted to OD=50 using gold diluent solution. 20% sucrose and 5% trehalose were added to the gold conjugate to stabilize the goat anti-Nov9X phytase antibody (0.2 g sucrose and 50 mg trehalose per 1 ml gold conjugate) and was mixed until completely dissolved. A polyester sheet was sprayed with the gold conjugated anti-phytase antibody using a Camag™ volume to 27 (1.5 µl/cm). The polyester sheet was placed on the platform and secure with the magnets. The sheet was sprayed with the conjugate, moving 9 mm for each run, until the entire polyester sheet was filled. Eight lines of conjugate will fill a sheet. The sheet was dried at 37° C. for 1 hr. Then Cut the sheet into ¼" strips such that the line of gold conjugate runs along the top of each strip. Store desiccated at RT.

Phytase Strips—Assembly

Materials
1. Cards coated with chicken anti-phytase IA-P antibody at 1.0 mg/ml and 1 µl/cm.
2. ⅝"×180 mm strips of #40 absorbant paper (top pad)
3. ¾"×180 mm strips of #903 paper treated with solution C, pH 8.6 (bottom pad).
4. ¼"×180 mm strips of sprayed gold conjugate (goat anti-NOV9X, OD=50 at 1.5 µl/cm).

Procedure

Note: Strips are assembled under conditions of less than 40% humidity. Wear gloves to apply all components. Two liners are removed from the glue strips at the bottom of the card. The gold strip was positioned with the line of gold conjugate along the top and overlapping the membrane by 1-1.5 mm. The bottom pad was placed along the bottom edge of the card, taking care to leave the gold strip exposed. The liner was removed form the glue strips along the top of the card. Place the top pad along the top of the card overlapping the membrane by 1-1.5 mm. The finished cards were stored desiccated at RT until ready for cutting into strips.

The strips were cut into 4 mm lengths. One card will yield ~40 strips. Store strips desiccated at room temperature.

Example 3

Detection of Enzymatically Active Phytase

Procedure

Figure 2:
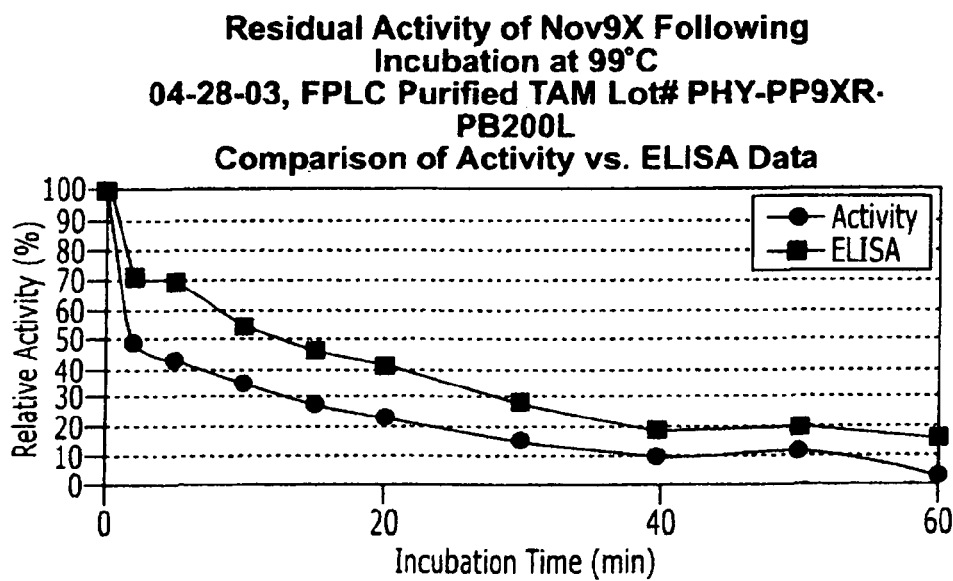
FIG. 2 is a graph showing the percent relative activity versus incubation time at 99° C. of the phytase enzyme in both an ELISA and an enzyme-activity assay. The detection of phytase enzyme in the ELISA parallels the amount of activity detected in the enzyme-activity assay.

*Pichia* produced purified phytase was inactivated by heating to 99° C. for up to 60 minutes. The phytase was then tested for enzyme activity and compared to reactivity in the phytase ELISA (FIG. 2) and reactivity with the phytase immunostrips (FIG. 3). ELISA comparison: FIG. 2 shows a graph of the Residual activity of Nov9X following incubation at 99° C. 04-28-03, FPLC purified TAM Lot # PHY-PP9XR-PB200L Comparison of Activity vs. ELISA Data. This demonstrates that the ELISA assay and the immunostrips appear to detect active phytase only. Phytase inactivated by heating is not detected in either assay.

Example 4

Phytase Immunoassay Kit

This diagnostic test (see FIG. 4) was designed for the rapid (10 min) detection of phytase in feed. The kit contains all reagents and equipment needed to perform the test. The kit can be stored at ambient temperatures not exceeding 100° F. (38° C.). The tests are packaged in a sealed moisture-proof foil bag with a silica gel desiccant capable of absorbing some moisture. Keep the test in its package until prior to its use. Avoid placing the test in a damp place.

Assay Procedure
1. Fill the large tube with feed up to the 15 mark. Add this amount of feed to one side of the mesh insert within the extraction bag.
2. Remove one plastic container of extraction buffer (25 ml) from kit and pour into the extraction bag.
3. Close bag and gently move the buffer over the feed to ensure that all the feed is wet. Wait at least 10 minutes.
4. Remove a Field Test from the foil bag and place on a flat dry surface. Check the desiccant. It should be blue. If it is pink, the tests are no longer valid and should be discarded.
5. Using the transfer pipet, transfer 3-5 drops of the feed extract to fill the sample well of the field test.
6. Wait approximately 5 minutes for the results to appear in the window above the sample well.

Results

If phytase is present in the sample, a double red line appears in the result window of the field test. The lower line indicates the presence of phytase, while the upper line is the control line signaling a properly working device. The test line will not be as strong as the control line. Any reaction seen at the test line is considered positive.

If no phytase is present, only one single red control line appears in the result window.

Example 5

Detection of Phytase in Pelleted Feed

This example demonstrates the use of the immunostrip assays to detect phytase in pelleted animal feed.

The methods and reagents are described as above in Example 4, with the exception that the pelleted animal feed is crushed to a grainy or powdery consistency with any menchanical device, and that the extraction buffer was 5% methanol with 0.5% Tween-20 in water instead of the borate buffer. Also, the anti-phytase antibody was from chicken instead of rabbit. The results are set forth below in Tables 4 and 5. Tables 4 and 5 show that Quantum® phytase was detectable in both mashed or starter diets (before pelleting) and pelleted or crumbled diets using the ELISA assay. In Table 5, activity was also confirmed with the enzyme activity assay. Results for both Tables 4 and 5 was also confirmed by immunostip assay (results not shown).

TABLE 4

Detection of Phytase in Pelleted or Mash Feed

| Diet | ELISA Result ng/ml | Phytase Level Added | Type |
|---|---|---|---|
| RA0309 Starter Diet 1 | 0 | 0 | mash |
| RA0309 Starter Diet 9 | 0 | 0 | pellet |
| RA0309 Starter Diet 4 | 0 | 0 | mash |
| RA0309 Starter Diet 15 | 0 | 0 | pellet |
| RA0309 Starter Diet 11 | 22.3375 | 285 | mash |
| RA0309 Starter Diet 19 | 24.9875 | 285 | mash |
| RA0309 Starter Diet 2 | 8.8425 | 285 | pellet |
| RA0309 Starter Diet 23 | 10.93 | 285 | pellet |
| RA0309 Starter Diet 6 | 27.495 | 566 | mash |
| RA0309 Starter Diet 17 | 46.25 | 566 | mash |
| RA0309 Starter Diet 13 | 19.76 | 566 | pellet |
| RA0309 Starter Diet 21 | 24.425 | 566 | pellet |
| RA0309 Starter Diet 3 | 58.19 | 1133 | mash |
| RA0309 Starter Diet 14 | 69.0275 | 1133 | mash |
| RA0309 Starter Diet 7 | 20.7225 | 1133 | pellet |
| RA0309 Starter Diet 22 | 32.825 | 1133 | pellet |
| RA0309 Starter Diet 12 | 153.62 | 2832 | mash |
| RA0309 Starter Diet 24 | 173.7425 | 2832 | mash |
| RA0309 Starter Diet 10 | 104.2125 | 2832 | pellet |
| RA0309 Starter Diet 28 | 100.6525 | 2832 | pellet |
| RA0309 Starter Diet 5 | 0 | 305 | Ronozyme |
| RA0309 Starter Diet 26 | 0 | 605 | Ronozyme |

TABLE 5

Phytase Activity and ELISA quantitation of Phytase in Starter and Crumbled Diets

| | Extractable Activity Average (FTU/kg) | ELISA Result ng/ml |
|---|---|---|
| Starter Diets | | |
| T1 | 37.7 | 0.0 |
| T2 | 301.1 | 4.9 |
| T3 | 426.3 | 16.7 |
| T4 | 74.8 | 0.0 |
| T5 | 209.8 | 7.5 |
| T6 | 449.3 | 17.3 |
| T7 | 58.0 | 0.0 |
| T8 | 152.7 | 4.0 |
| T9 | 806.6 | 13.3 |
| T10 | 436.5 | 18.4 |
| Crumbled Diets | | |
| T1 | 50.6 | 0.0 |
| T2 | 142.2 | 4.5 |
| T3 | 353.7 | 11.4 |
| T4 | 68.7 | 0.0 |
| T5 | 167.7 | 12.7 |
| T6 | 237.8 | 9.1 |
| T7 | 50.4 | 0.9 |
| T8 | 234.4 | 8.8 |
| T9 | 301.7 | 13.6 |
| T10 | 711.0 | 22.5 |

Example 6

Production of Monoclonal Antibodies to Phytase

Monoclonal antibodies against phytase were generated using a method based on the one initially described by Kohler G., Milstein C. Nature 256, 495-497 (1975). Mice (Alderley Park strain) were immunised with phytase protein (Ref. *Pichia pastoris* NOV 9X Oct. 13, 2003). Three 20 μg doses were delivered by sub-cutaneous injection at two-week intervals. Dose one included Freund's complete adjuvant; dose two and three included Freund's incomplete adjuvant. At least six weeks after the third dose mice were boosted with 20 μg doses of phytase delivered intra-venously without adjuvant. Spleens were harvested four days after the intra-venous boost. Lymphocytes were washed from the spleens with Dulbecco's Modified Eagle's Medium (DMEM) delivered by syringes with 20-gauge needles.

NS0 myeloma cells (HGPRT-) were obtained from the European Collection of Cell Cultures. The myeloma cells were cultured in DMEM containing 584 mg/L L-glutamine, 13.6 mg/L hypoxanthine, 3.88 mg/L thymidine and 10% foetal bovine serum (FBS) at 37° C. in 5% $CO_2$. Myeloma cells were selected for fusion when at a density of around $5 \times 10^5$/ml.

Lymphocytes from a single spleen (approximately $2 \times 10^8$) were mixed with $2 \times 10^7$ NS0 myeloma cells. The cell mixture was pelleted by centrifugation and the supernatant was decanted. The cell pellet was gently resuspended and then fused by the dropwise addition of 1 ml of a 50% polyethylene glycol (1500) in HEPES buffer pH8 over one minutes Complete culture medium (DMEM containing L-glutamine, hypoxanthine, thymidine and FBS) was then added slowly over several minutes to a final volume of 50 ml. The resulting fusion was then plated out into 96-well tissue culture plates. Several hours later, fusion wells were topped up with an equal volume of complete medium also containing hypoxanthine, thymidine and 0.352 mg/L aminopterin.

Approximately two weeks post-fusion the culture supernatants were assayed for the presence of phytase-specific antibodies using an antibody capture enzyme-linked immunosorbant assay (ELISA) based on the method described by Engvall E., and Perlmann P. Immunochemistry 8, 871-874 (1971); and Harlow E. et al., Antibodies—A Laboratory Manual, Cold Spring Harbor Laboratory, (1988) pp. 182-183.

In addition, culture supernatants were also assayed by Biacore®, a biomolecular interaction analysis technique using surface plasmon resonance technology, to select antibodies able to capture phytase from solution and also detect pairs of antibodies able to bind simultaneously to phytase. The method was developed from one described by Fägerstam L. et al., J. Mol. Recognition 3, 208-214 (1991).

Selected hybridoma cells were then taken through at least two rounds of cloning by limiting dilution followed by re-assay, to ensure both clonality and stability of the hybridomas. Banks of frozen hybridomas were prepared.

Production of selected monoclonal antibodies was achieved by scaling-up tissue culture. The antibodies were purified from culture supernatants by affinity chromatography using protein G Sepharose using a standard method as described in the Antibody Purification Handbook published by Amersham Biosciences (part of GE Healthcare).

Example 7

Monoclonal Antibody Immunostrip

The lateral-flow immunostrip comprised a detection membrane of nitrocellulose (2.5×18 cm), supported on a plastic backing, in which a 1 mm line of anti-phytase monoclonal antibody from one of cell lines #PHY36 (ACC2699), #PHY37 (ACC2700), or #PHY46 (ACC2701) was sprayed. A reagent control line of donkey anti-mouse antibody was sprayed in parallel above the first antibody line. The bottom end portion of the strip of nitrocellulose is over-layered with a piece of polyester strip. The polyester strip is first treated with 0.5% BSA, 0.5% polyvinylalcohol and 0.1% Triton X-100; 50 mM phosphate buffer pH 7.4 and the colloidal gold conjugated anti-phytase monoclonal antibody from #PHY34 (ACC2698) (antibody conjugated to 40 nm colloidal gold by Capricorn Products, Inc., Portland, Me.). The polyester strip is allowed to dry. The polyester strip is then over-layered with a sample application pad of cotton. The sample application pad was also pre-treated with 0.1% Triton X-100 and 0.1 M borate buffer pH 8.5 and allowed to dry. Flanking the other end or top end of the nitrocellulose strip is another cotton pad to absorb the solution from the sample after it passes over the test antibody and control antibody areas on the nitrocellulose. This completed card was then cut into 4 mm test strips to fit into a plastic cassette with an oval sample application well positioned above the sample pad and a rectangular detection window positioned above the detection area of the nitrocellulose membrane.

Figure 5:
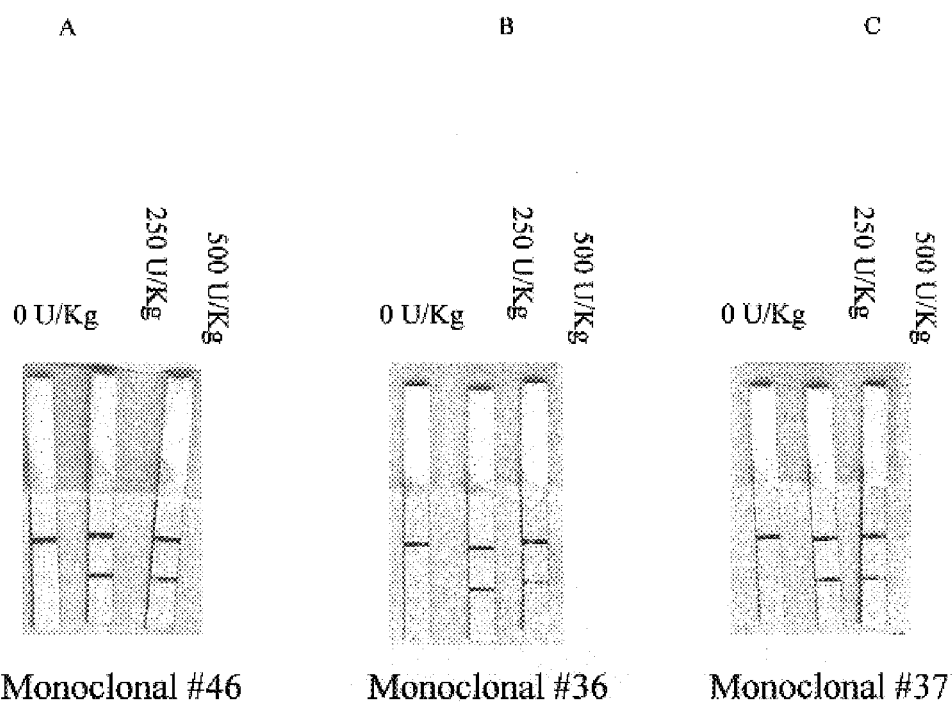
FIGS. 5A-C are a series of three immunostrips showing a comparison of coating anti-phytase monoclonal antibodies and their ability to detect phytase from test samples of phytase-containing corn feed at concentrations of 0 U/Kg; 250 U/Kg; or 500 U/Kg.

FIG. 5 demonstrates that all three lines of monoclonal antibodies, PHY46, PHY36 and PHY37 were able to detect phytase enzyme in phytase-containing corn feed samples. Monoclonal anti-phytase antibody PHYMAb 28 did not function in the immunostrip assay (data not shown).

Example 8

Monoclonoal Antibody Reactivity to Various Phytase Proteins

This example demonstrates the difference in the reactivity of the monoclonal anti-phytase antibody to different phytase enzymes from bacterial or fungal sources. The immunostrips were prepared and performed as described above in Example 7. Monoclonal anti-phytase antibody PHY37 was used as the coating antibody and PHY34 was used as the labeled antibody (labeled with colloidal gold). Samples of other commercial phytase enzymes were used as samples including: Ronozyme®, Phyzyme® and Natuphos®.

Figure 6:
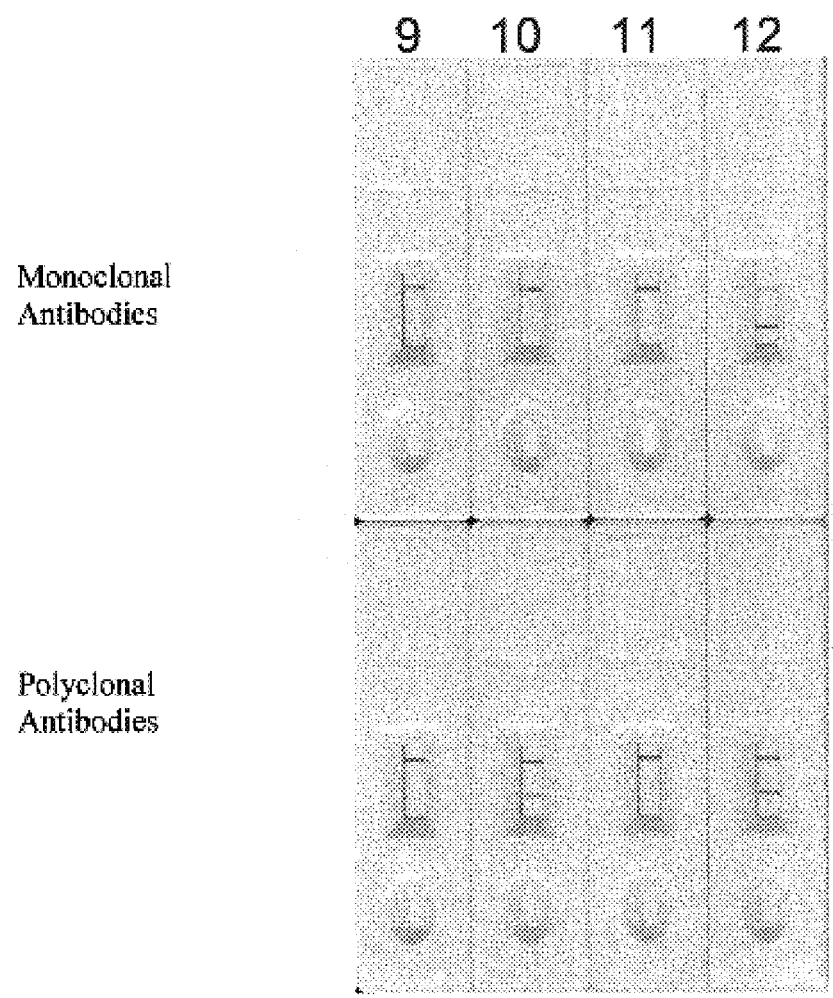
FIG. 6 is a comparison of Phytase Immunostrip assays using either monoclonal anti-phytase antibodies (top row) or polyclonal anti-phytase antibodies (bottom row). Phytase enzyme samples in the sample lanes were: Lane 9—Ronozyme®; lane 10—Phyzyme®; lane 11—Natuphos®; and lane 12—Quantum™ Phytase.

The results in FIG. 6 demonstrate that the immunostrips made with polyclonal anti-phytase antibodies detect Quantum™ phytase and Phyzyme® which are phytase enzymes derived from *E. coli*, but did not detect phytase enzymes derived from fungi such as Ronozyme® and Natuphos®. The immunostrips made with monoclonal anti-phytase antibodies only detect Quantum™ phytase.

Example 9

Monoclonal Antibody ELISA

This example describes the detection and quantitative measurement of phytase enzyme in a corn sample using monoclonal antibodies in the ELISA immunological technique.

The multiwell plates (Nunc, Maxisorp) were coated at 4° C. overnight with the monoclonal #46 (cell line PHY46— ACC2701) anti-phytase antibody at a concentration of 1 µg/ml, diluted in 50 mM sodium borate/boric acid, 75 mM NaClpH 8.5. The plates were washed five times with 10 mM Tris containing 0.05% Tween-20 and 0.03% sodium azide pH 8.0) (wash buffer). Note: the same wash step was performed after each incubation period to remove unbound antibodies/samples. Plates were then blocked for 45 min. at room temperature with 1% bovine serum albumin, 0.05% Tween-20, 0.03% sodium azide, 150 mM NaCl in 100 mM sodium phosphate, pH 7.4(diluent). On hundred microliters of each sample was added to the plate and incubated for 1.5 hr at room temperature. The biotinylated monoclonal PHY28 anti-phytase antibody (diluted to 1 µg/ml in diluent) was then added to the plates and incubated for 1 hr at 37° C. The detection antibody (alkaline phosphatase-labelled streptavidin was diluted to 2 µg/ml in diluent) was added to the plates and incubated for 1 hr at 37° C. The substrate, paranitrophenylphosphate (pNPP) was added and allowed to develop for 30 min at room temperature. The absorbance was measured at 405 nm with 492 nm as a reference.

Figure 7:
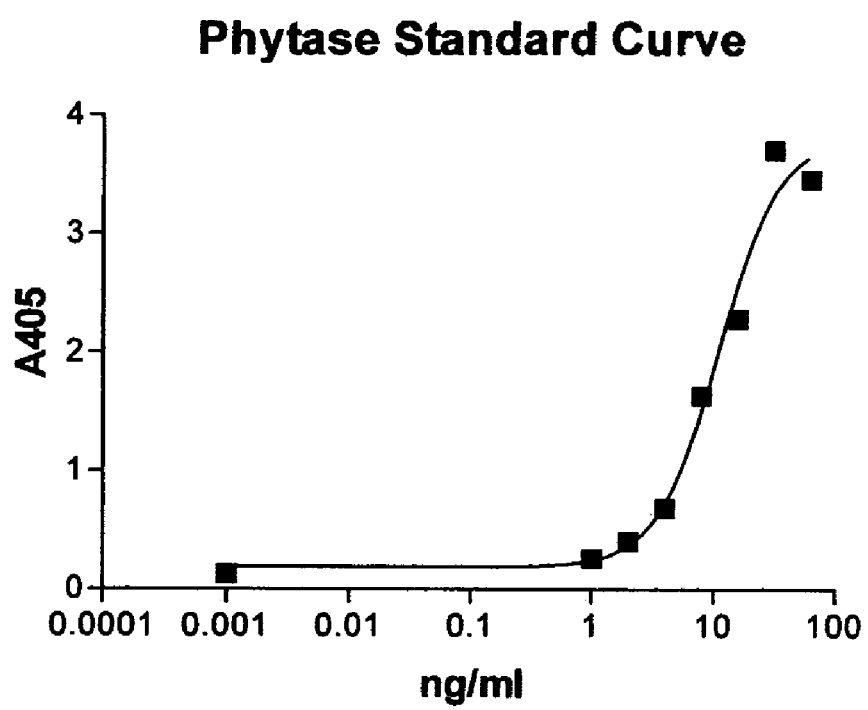
FIG. 7 is a standard curve of phytase present in samples tested using a Monoclonal antibody ELISA.
Figure 8:
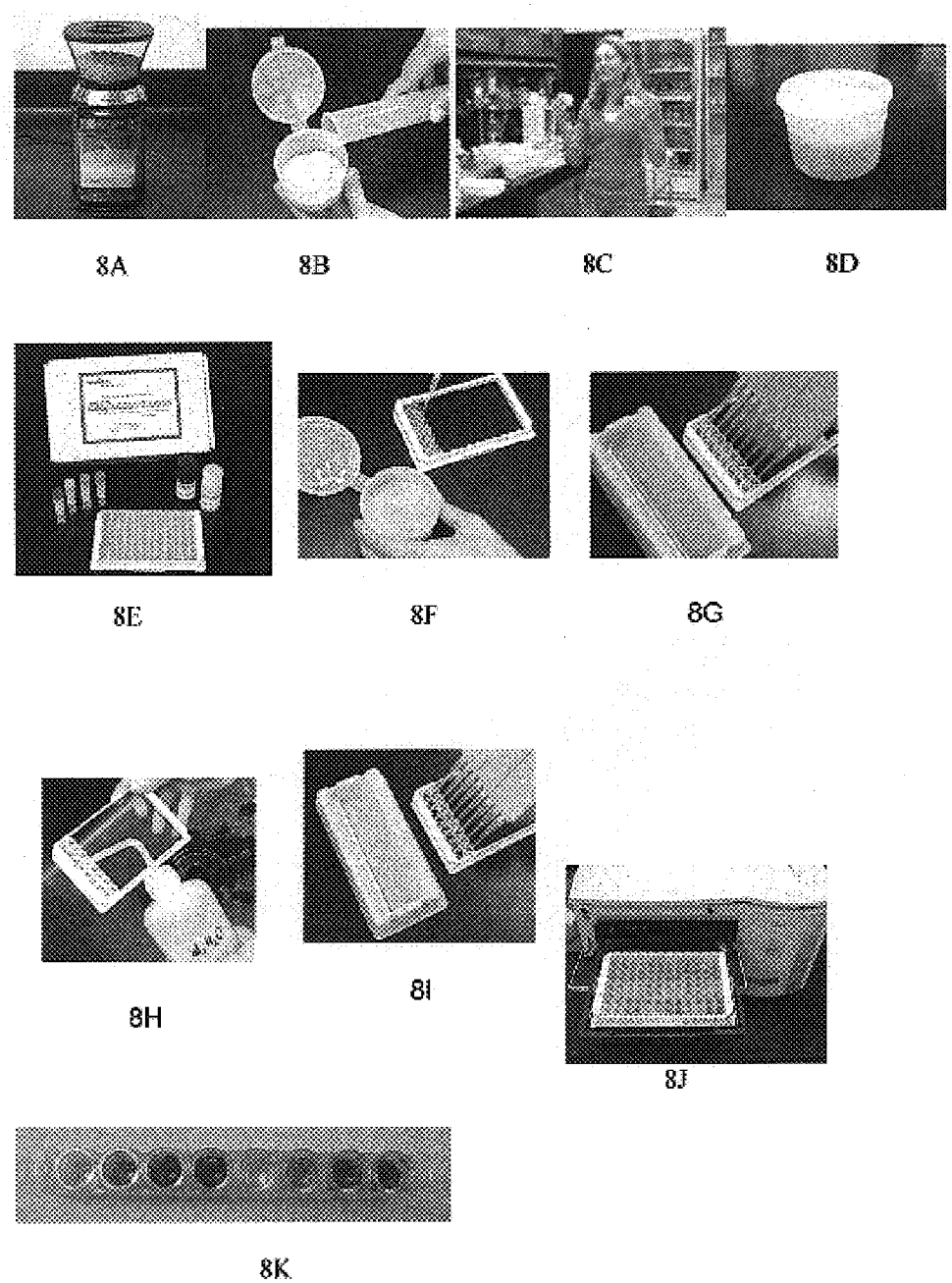
FIGS. 8A-K shows the steps for the Quick Quantum™ phytase ELISA.

The phytase standard curve produced the expected sigmoidal standard curve using a 4-parameter curve fit (see FIG. 7). The curve was plotted linear vs. log with a range from 0 to 64 ng/ml. To plot the 4-parameter standard curve on a log X axis, the 0 ng/ml standard must be entered into the analysis program at 0.001 ng/ml instead of 0 ng/ml. The analysis program used was WinSelect™ software for the Tecan Sunrise™ microplate reader, although any four-parameter curve-fitting program will work.

Example 10

Monoclonal Antibody Cross-reactivity with Other Phytase Enzymes

The monoclonal antibodies of the present invention were tested for their cross-reactivity to the fungal phytase enzyme, Ronozyme®, and for their specificity to Quantum™ phytase (Nov9X) using the ELISA assays described above in Example 9.

The results are set forth in Table 6. Monoclonal antibodies #36 and 37 cross reacted with the *E. coli* phytase (Phyzyme®). Mab #34 had no cross-reactivity with Phyzyme, but did react with Quantum™ phytase derived from the *E. coli* enzyme. Monoclonal antibodies #46 and #28 were also specific for Quantum™ phytase. None of the antibodies, including the polyclonal goat antibody, cross-reacted with either of the fungal phytase enzymes, Ronozyme® or Natruphos®.

For conducting immunoreactions using Mab #34, as the gold-labelled antibody, it would make the assay specific for Quantum™ phytase. Mab #46 and 28 could also be used to make an immunoassay specific for Quantum™ phytase.

TABLE 6

Percent Cross-reactivity of Monoclonal Antibodies to various Phytase enzymes

| Phytase | Mab 34 | Mab 36 | Mab 37 | Mab 46 | Mab 28 | Goat anti-Nov9X |
|---|---|---|---|---|---|---|
| Quantum ™ | 100% | 100% | 100% | 100% | 100% | 100% |
| Ronozyme ® | <0.01% | <0.01% | <0.01% | <0.01% | <0.01% | <0.01% |
| Phyzyme ® | <0.01% | 125% | 64% | <0.01% | <0.01% | 71% |
| Natruphos ® | <0.01% | <0.01% | <0.01% | <0.01% | <0.01% | <0.01% |

Example 11

Quick Quantum™ Phytase ELISA

This example describes the detection and semi-quantitative measurement of phytase enzyme in a feed sample using monoclonal antibodies in the ELISA immunological technique. The method and typical results are shown in FIGS. 8A-J.

The multiwell plates (Nunc, Maxisorp) were coated at 4° C. overnight with the monoclonal #46 (cell line PHY46—ACC2701) anti-phytase antibody at a concentration of 1 µg/ml, diluted in 50 mM sodium borate/boric acid, 75 mM NaCl buffered saline pH 8.5. The plates were washed five times with a Tris base buffer pH 8.0 (10 mM Tris containing 0.05% Tween-20 and 0.03% sodium azide pH 8.0). Plates were then blocked for 1 hr at room temperature with Stabil-Coat® (SurModics, Inc.) and dried for 18-24 hrs at 30° C. and 18% humidity. One hundred microliters of each sample was added to the plate and incubated for 15 min at room temperature. The plate was washed five times with distilled water and blotted on absorbent paper. Peroxidase conjugated monoclonal PHY28 anti-phytase antibody diluted to 1 µg/ml in 1% bovine serum albumin, 0.05% Tween-20, 0.04% Kathon CG® (Supelco, Inc.), 150 mM NaCl in 100 mM sodium phosphate, pH 7.4 was added to the plates and incubated for 15 min at room temperature. The substrate, 3,3',5,5'-tetramethylbenzidine (TMB) was added and allowed to develop for 15 min at room temperature. The absorbance was measured at 650 nm or visually compared to the controls.

Example 12

Phytase Extraction Kit

Intended Use

This extraction kit contains materials for the extraction of 20 feed samples. Distilled or deionized water is required but not provided.

Storage Requirements—Store kit at room temperature

Materials Provided
1. 20 extraction containers
2. 2 packets of borate buffer.
3. 2 bottles of 10 N sodium hydroxide (NaOH)
4. 2 tubes of 10% Tween-20
5. 1-50 ml tube
6. Directions for use Materials Recommended But Not Provided
1. Feed Grinder (Cuisinart CCM-16PC)
2. Scale capable of weighing 20 grams
3. 100 ml graduated cylinder
4. 1 liter container Precautions Carefully handle the sodium hydroxide solution. Gloves should be worn to avoid potential skin exposure.

Directions
1. Fill a suitable container with I liter of distilled or deionized water.
2. Add the contents of one packet containing sodium tetraborate.
3. Add the entire contents of one bottle containing sodium hydroxide (wear gloves).
4. Add the entire contents of one tube of Tween-20.
5. Mix thoroughly until all contents are dissolved completely.

Sample Extraction
1. Fill the Cuisinart burr coffee grinder with a 300 g representative sample and grind the entire sample until a particle size of a very fine instant coffee is achieved (finest setting on grinder).
2. Measure 20 g of ground feed sample and add to the extraction container. Alternatively, fill the 50 ml tube to the 35 ml mark, tap the tube on a flat surface to level the feed in the tube, and add to the extraction container.
3. Add 80 ml of extraction buffer or fill extraction container to the 1 10 ml mark. Shake thoroughly for 1 min. It is very important to shake the samples thoroughly for the entire minute in order to get consistent extractions.

4. Let sample sit for 30 minutes before testing to allow for settling of the insoluble particles.

Example 13

Quick Enzyme Detection Kit for Quantum™ Phytase

Introduction

This diagnostic kit is designed for the detection of Quantum™ phytase in feed. The test is an ELISA method in the standard microplate format (8×12 wells). The test is fast (45 minutes) as well as highly sensitive. It provides the examination of 44 samples in duplicate or of 88 samples in single determination. The kit also gives the flexibility of testing as few as 2-4 samples in 12 separate tests. The kit contains a negative and 3 positive control samples.

Principle of the Test

The wells of the solid phase are coated with an antibody that specifically recognizes Quantum™ phytase.

$1^{st}$ reaction: Quantum™ phytase present in the sample is bound to the immobilized antibody, forming the antigen-antibody complex. A second antibody, directed to Quantum™ phytase, binds to the antigen-antibody complex. This antibody (the conjugate) is labeled with horseradish peroxidase.

$2^{nd}$ reaction: The enzyme labeled antigen-antibody complex converts a substrate into a blue product. Samples containing Quantum™ phytase exhibit the blue color development, whereas samples without Quantum™ phytase remain colorless.

Storage Requirements

The kit is stable until the expiration date stated on the label when stored refrigerated at 2-8° C.

Materials Provided 7. 96 antibody-coated microwells
8. 4 bottles of 0.7 ml each 0, 200, 400, and 800 units/Kg Quantum™ phytase controls
9. 1 bottle of 6 ml HRP conjugate solution
10. 1 bottle of 6 ml TMB substrate solution Materials Recommended But Not Provided 5. Extraction Kit
6. Scale capable of weighing 20 grams
7. 100 ml graduated cylinder
8. Feed Grinder (Cuisinart CCM-16PC)
9. Squirt bottle for distilled/deionized water
10. 1- and 8-channel pipettes for 50 and 100 µl
11. Pipette tips
12. Microplate photometer fitted with a 650 nm filter Sample Extraction 5. Fill the Cuisinart burr coffee grinder with a 300 g representative sample and grind the entire sample until a particle size of a very fine instant coffee is achieved (finest setting on grinder).
6. Measure 20 g of ground feed sample and add to an extraction container.
7. Add 80 ml of extraction buffer (25 mM Borate pH 10.0 containing 0.01% Tween-20). Shake thoroughly for 1 min. It is very important to shake the samples thoroughly for the entire minute in order to get consistent extractions.
8. Let sample sit for 30 minutes before testing to allow for settling of the insoluble particles.

Assay Procedure

Allow all reagents to warm to room temperature (1 8-30° C.) before use (approximately 30 min).

1. Remove the microtiter plate from the foil bag. Remove rows of wells that are not needed for the test and return to the foil bag. Seal the bag to keep the unused wells dry.
2. Using a pipet, transfer the controls and the prepared extracts into the wells of the plate; 50 µl per well. Using an 8-channel pipet, dispense HRP conjugate solution at 50 µl per well to all wells of the plate. Mix contents of wells by gently shaking the plate back and forth on a flat surface for 10-20 seconds without splashing reagents from the wells. Incubate for 30 min at room temperature.
3. Empty the contents of the wells. Wash all wells by filling the wells with distilled/deionized water and then shaking out the contents. Repeat this 5 times, and then tap the plate firmly on several layers of paper towels to remove residual water.
4. Using an 8-channel pipet, dispense the TMB substrate solution (amber bottle) to all wells of the plate at 100 µl per well. Incubate for 15 min at room temperature.
5. Read the optical density at 650 nm or visually compare sample wells to control wells.

Result Analysis

The assay is operating properly if the controls (200, 400, and 800 units/Kg) exhibit a blue color with gradually increasing intensity and the negative control remains colorless. Contact your Syngenta representative if you have any questions concerning the assay performance.

Modifications of the present reagents, methods and kits for detecting feed enzyme proteins, in particular phytase, will be obvious to those skilled in the art from the foregoing detailed description.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

Numerous patents, applications and references are discussed or cited within this specification, and all are incorporated by reference in their entireties.

What is claimed is:

1. A monoclonal antibody that reacts specifically with a Nov9X phytase.

2. The monoclonal antibody of claim 1 which is produced by hybridoma cell line PHY36 deposited as DSM ACC2699, or cell line PHY37 deposited as DSM ACC2700.

3. The monoclonal antibody of claim 1 which is produced by the hybridoma cell line PHY34 deposited as DSM ACC2698; cell line PHY46 deposited as DSM ACC2701 or cell line PHYTASE MAb28 deposited as DSM ACC2715.

4. An antigen binding fragment of the monoclonal antibody of claim 1.

5. The antibody of claim 1 which has been labeled.

6. The antibody of claim 5 which has been labeled with biotin, peroxidase, alkaline phosphatase, glucoamylase or β-galactosidase.

7. The antibody of claim 5 which has been labeled with $I^{125}$, $I^{131}$ or tritium.

8. A solid support to which the antibody of claim 1 has been attached.

9. A composition comprising the monoclonal antibody of claim 1 and a buffer or diluent.

10. A hybridoma cell line which produces the monoclonal antibody of claim 1.

11. The hybridoma cell line of claim 10 wherein the cell line is PHY36 deposited as DSM ACC2699 or cell line PHY37 deposited as DSM ACC2700.

12. The hybridoma cell line of claim 10 wherein the cell line is PHY34 deposited as DSM ACC2698; cell line PHY46 deposited as DSM ACC2701 or cell line PHYTASE MAb28 deposited as DSM ACC2715.

13. An immunoassay for the detection of a Nov9X phytase comprising:
   a) contacting the anti-Nov9X phytase specific monoclonal antibody of claim 1 with a sample suspected of containing the phytase for a time and under conditions suitable for binding of the anti-Nov9X phytase specific antibody to the Nov9X phytase,
   b) determining binding between the anti-Nov9X phytase specific antibody and Nov9X phytase, and
   c) relating the binding to the presence or amount of the Nov9X phytase in the sample.

14. The immunoassay of claim 13 which is a RIA.

15. The immunoassay of claim 13 which is an EIA.

16. An immunoassay for the detection of a Nov9X phytase in a sample comprising the steps of:
   a) preparing an extract of the sample in the presence of the anti-Nov9X phytase specific monoclonal antibody of claim 1 which immunologically recognizes the Nov9X phytase in the extract such that an anti-Nov9X phytase specific antibody-Nov9X phytase complex is formed;
   b) preparing a solid phase format having a measurement in three dimensions to form a volume with a plurality of interstitial spaces by binding to the solid phase format a desired second antibody capable of immunologically recognizing the Nov9X phytase;
   c) combining the extract of step (a) with the prepared format of step (b) whereby the extract is drawn through the interstitial spaces of the prepared solid phase format capturing the anti-Nov9X phytase specific antibody-Nov9X phytase complex;
   d) detecting the Nov9X phytase by the presence of said captured anti-Nov9X phytase specific antibody-Nov9X phytase complex.

17. The immunoassay of claim 16 wherein the solid phase format is cellulose acetate, cellulose, nitrocellulose or nylon.

18. The immunoassay of claim 17, wherein the solid phase format is composed of multiple stacked and contiguous layers wherein each layer is capable of capturing a different phytase.

19. The immunoassay of claim 18, further comprising a sample absorption pad of the solid phase format.

20. The immunoassay of claim 19 further comprising a strip comprising a labelled anti-phytase antibody.

21. The immunoassay of claim 20 wherein the means of detection is colloidal gold.

22. A kit for detection by the immunoassay of claim 19 comprising:
   a) a means of extraction of the phytase from a sample; and
   b) a solid phase format comprising the anti-Nov9X phytase specific monoclonal antibody of claim 1 and having a measurement in three dimensions to form a volume with a plurality of interstitial spaces by binding to the solid phase format a desired second antibody capable of immunologically recognizing the Nov9X phytase.

23. The kit of claim 22 further comprising a vessel containing a buffer.

24. The kit of claim 23 further comprising a means of dispensing the sample onto the solid phase format.

25. An immunoassay for the detection and quantification of a Nov9X phytase comprising the steps of:
   a) preparing an extract of a sample;
   b) incubating a portion of the extract with the anti-Nov9X phytase specific monoclonal antibody of claim 1 which binds to the Nov9X phytase, the Nov9X phytase specific antibody being bound to a solid carrier, and a second anti-phytase antibody which binds to the phytase bound by the anti-Nov9X phytase specific antibody to create an antibody-phytase-antibody complex,
   c) washing the antibody-phytase-antibody complex to remove unbound second antibody;
   d) adding a detection antibody that immunologically reacts with the second antibody wherein the detection antibody is labelled; and
   e) measuring the amount of bound or unbound labeled detection antibody to determine the concentration of Nov9X phytase.

26. The immunoassay of claim 25 wherein the detectable label is an enzyme.

27. The immunoassay of claim 26, wherein the enzyme is alkaline phosphatase, peroxidase, or β-galactosidase.

28. The immunoassay of claim 27, wherein the enzyme produces an insoluble reaction product.

29. A kit for the detection and quantification by the immunoassay of claim 25 comprising:
   a) a means of extracting the phytase from a sample;
   b) a solid support comprising an anti-Nov 9X phytase specific antibody bound to the solid support;
   c) a second anti-Nov9X phytase antibody; and
   d) a detection antibody capable of immunologically binding to the second antibody and wherein the detection antibody is labelled with a detectable label.

30. The kit of claim 29 wherein the detectable label is an enzyme.

31. The kit of claim 30 wherein the detection enzyme is alkaline phosphatase, peroxidase, or β-galactosidase.

32. The kit of claim 31 wherein the enzyme produces a soluble or an insoluble reaction product.

33. The kit of claim 32 further comprising a substrate for the enzyme.

* * * * *